US00PP18282P3

(12) United States Plant Patent
Dirr

(10) Patent No.: US PP18,282 P3
(45) Date of Patent: Dec. 4, 2007

(54) ***HYDRANGEA MACROPHYLLA* PLANT NAMED 'HYMMAD II'**

(50) Latin Name: *Hydrangea macrophylla*
Varietal Denomination: HYMMAD II

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 83 days.

(21) Appl. No.: 11/348,534

(22) Filed: Feb. 6, 2006

(65) Prior Publication Data

US 2007/0186318 P1 Aug. 9, 2007

(51) Int. Cl.
*A01H 5/00* (2006.01)

(52) U.S. Cl. ..... Plt./250

(58) Field of Classification Search ..... None
See application file for complete search history.

(56) References Cited

U.S. PATENT DOCUMENTS

PP17,169 P3 * 10/2006 Dirr ..... Plt./250
2006/0212982 P1 * 9/2006 Dirr ..... Plt./250

* cited by examiner

*Primary Examiner*—Wendy C. Haas
(74) *Attorney, Agent, or Firm*—Greenlee Winner and Sullivan PC

(57) ABSTRACT

*Hydrangea macrophylla,* 'Hymmad II' has multi-rowed pink lacecap inflorescences that maintain the color in the presence and absence of aluminum. Inflorescences mature to a beautiful lime green. The habit is rounded with strong purple-black stems that hold the flowers upright. The lustrous, leathery, bullate, black-green leaves are highly mildew resistant.

4 Drawing Sheets

Botanical classification: *Hydrangea macrophylla.*
Varietal denomination: 'Hymmad II'.

BACKGROUND OF THE INVENTION

The present invention relates to a new and distinct cultivar of *Hydrangea macrophylla,* a member of the Hydrangeaceae family, hereinafter referred to as 'Hymmad II'. This cultivar is grown primarily as an ornamental for landscape use and for use as a potted plant, fresh cut and dried flowers. The cultivar originated from open-pollination of *Hydrangea macrophylla* 'Nigra' (also know as 'Mandschurica') (non-patented, the pollen donor being unknown. It was selected at the University of Georgia, Athens, Ga. in 2002, from the progeny seedlings of this open pollination by continued evaluation for large, triple-rowed, pink sepals surrounding the center of fertile, violet-purple flowers, stout purple-black stems, increased mildew resistance, and improved leaf and flower characteristics.

'Hymmad II' is distinguished from its female parent 'Nigra', which has a pink or blue mophead inflorescence, by its pink lacecap inflorescence that does not change color in the absence or presence of aluminum (Al). The sepals (sterile florets) emerge green around the periphery of the inflorescence, open pink, and mature to lime green, maintaining the latter color when utilized as dried flowers. Inflorescences are more resistant to water stress and do not wilt under high heat. 'Hymmad II' has lustrous, more leathery, bullate, black-green leaves than 'Nigra'. 'Hymmad II' had slight mildew in early fall, whereas in side-by-side comparisons, 'Nigra' was 100% infected by mildew. The thick, stout stems of 'Hymmad II' hold the inflorescence upright, without splaying. 'Nigra' inflorescences are mopheads and weigh the stems to the ground. 'Hymmad II' produces flowers from terminal and lateral buds, whereas 'Nigra' only produces them from terminal buds.

SUMMARY OF THE INVENTION

The following traits have been observed and represent the characteristics of the new Cultivar. In combination these characteristics distinguish 'Hymmad II' from all other varieties in commerce known to the inventor.

1) Pink-mauve flowers (sepals) are not affected by the presence or absence of Al and hold the color until maturation.
2) At maturation, sepals turn lime green and dry to this color.
3) Triple rows of sepals around the periphery of the inflorescence create a showier lacecap than typical for the species.
4) Inflorescences are more resistant to heat and drought and do not wilt under moderate stress.
5) Leaves are more heat and drought resistant than 'Bailmer' U.S. Plant Pat. No. 15,298) and, growing side-by-side do not flag (wilt) like the latter.
6) Rounded habit with thick, stout purple-black stems that hold the inflorescences upright.
7) Lustrous, leathery, bullate, black-green leaves.
8) Leaves display high mildew resistance. 'Nigra', in Athens, Ga., is typically defoliated by powdery mildew in October while 'Hymmad II' is completely foliated with only slight mildew on the older leaves.

'Hymmad II' has been asexually propagated in Athens, Ga. since 2002. The characteristics of the cultivar have been stable and reproduced true-to-type in successive vegetative generations.

BRIEF DESCRIPTION OF THE PHOTOGRAPHS

BOTANICAL DESCRIPTION OF THE PLANT

Figure 1:
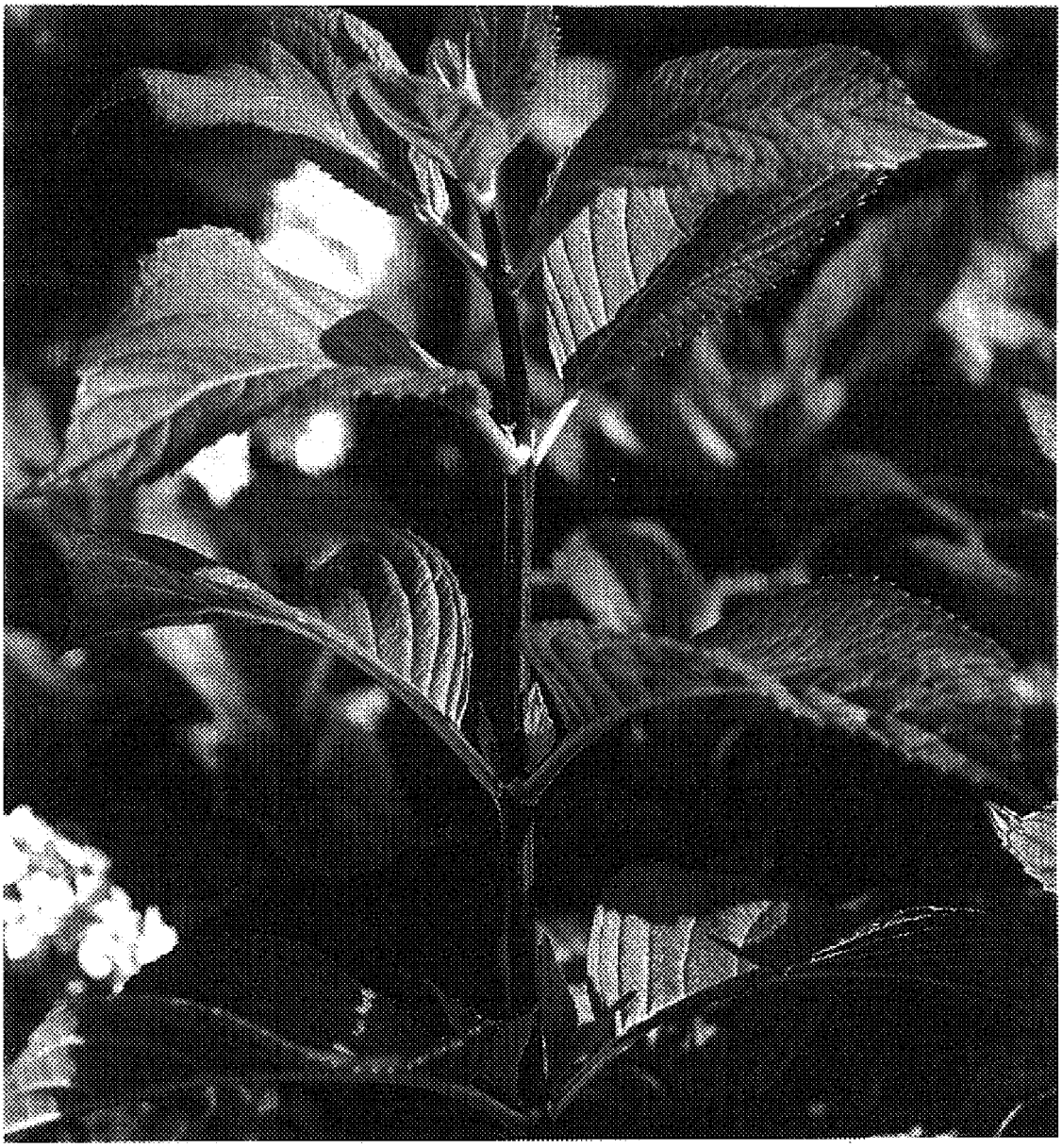
FIG. 1 shows lustrous black-green leaves on thick, purple-black stem.
Figure 2:
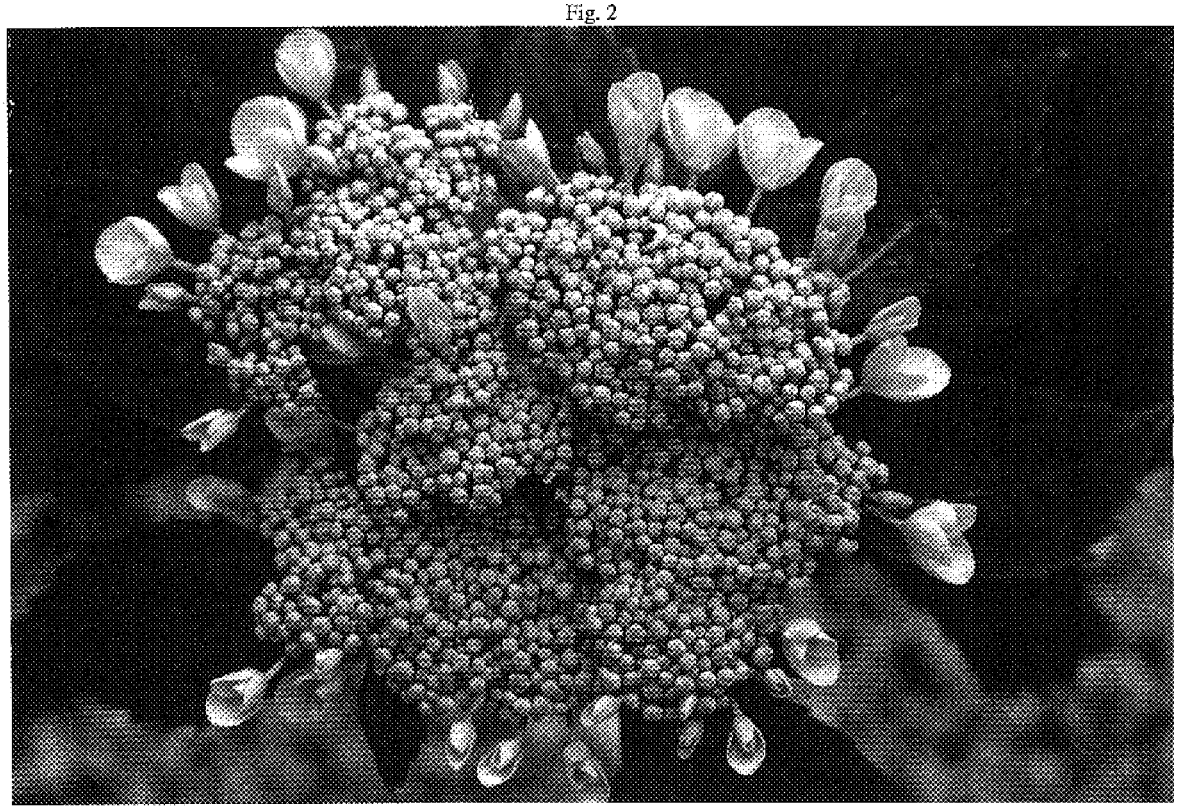
FIG. 2 shows inflorescence opening showing emerging green sepals and green-pink fertile flower buds.
Figure 3:
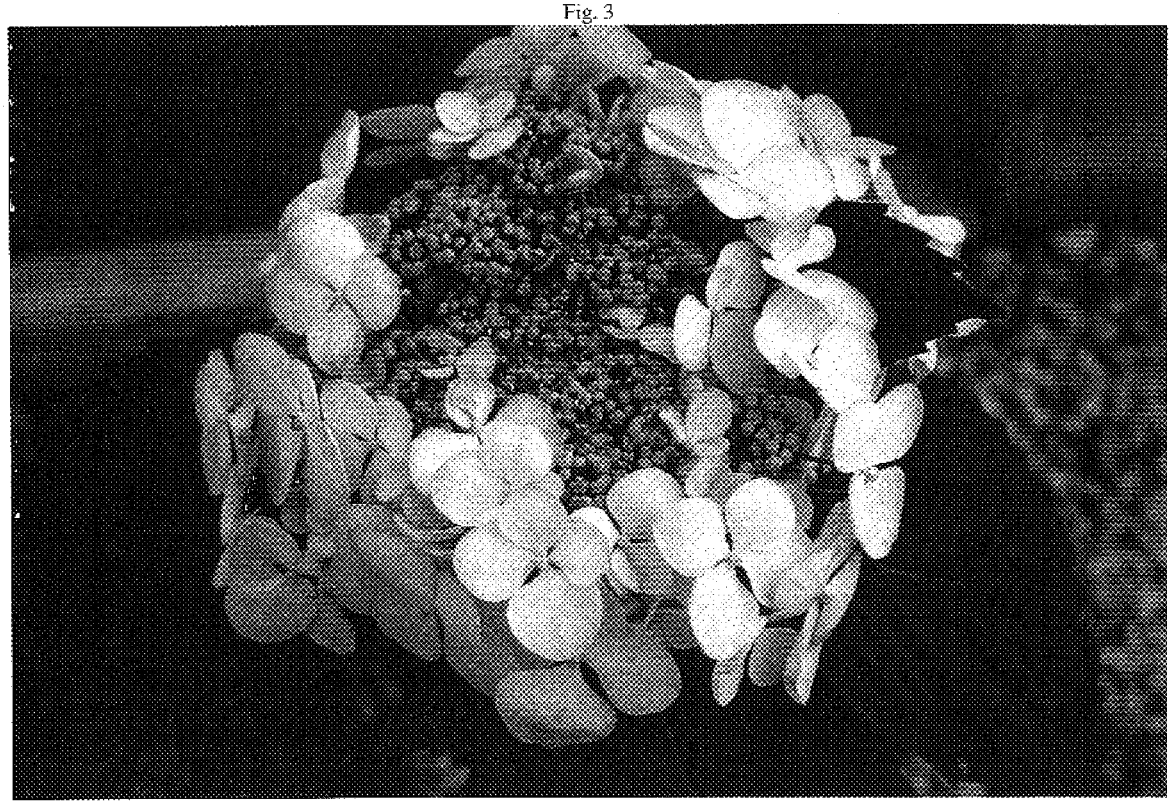
FIG. 3 shows peak inflorescence showing triple-rowed pink sepals and green-purple fertile flower buds.
Figure 4:
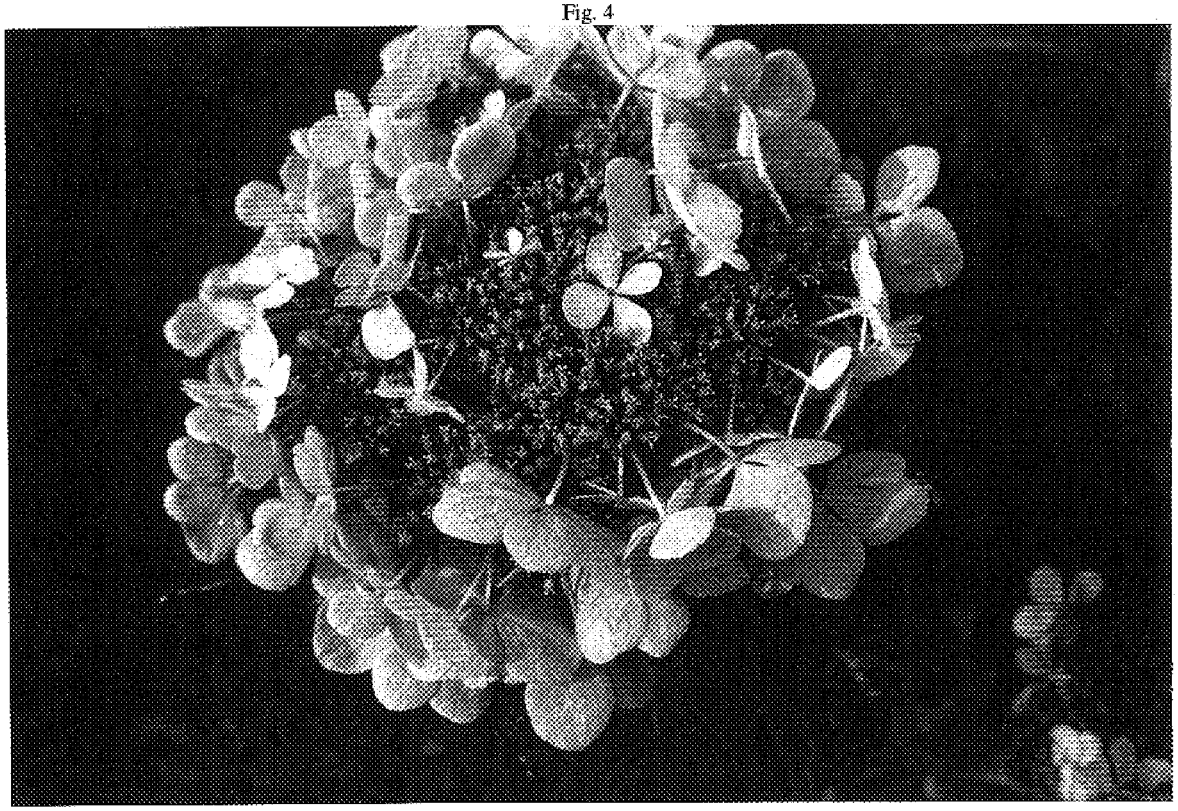
FIG. 4 shows inflorescence with maturing green sepals.

A detailed description of *Hydrangea macrophylla* 'Hymmad II' follows. Colors are based on The Royal Horticultural Colour Chart (1995). All measurements/characteristics were taken from 2-year-old plants growing in 11.8 liter containers under 50% shade at Athens, Ga., USDA Zone 7. Measurements of leaf/stem and floral characteristics are based on 10 to 20 samples. The presence of Al means that the plant was treated with aluminum sulphate (42 g per 3.8 liters of water) applied as a soil drench when flower buds were visible.

Plant: The plant has an upright, rounded growth habit, with many upright branches from the base, attaining a size of 30 cm high by 60 cm wide after 2 years.

Stems: Current year stems are round, averaging 5 mm in diameter, with no pubescence, and are Greyed-Purple 187A in color. The average internode length is 10.5 cm. Second year stems are round, 10 mm in diameter, not pubescent and Greyed-Yellow 161D, Greyed-Orange 165B, Greyed-Brown N199C in color.

Vegetative buds: The willow type vegetative buds are in an opposite arrangement, 2 per node, at a 45° angle to the stem. They are globose in shape, 8 mm by 4 mm, and have 2 scales which are Greyed-Brown 199C in color. The bud color is Greyed-Purple 183B.

Flower buds: The flower buds are round in shape with no pubescence, 4 mm long by 4 mm wide by 3 mm deep and Violet-Blue 98C in presence of Al, and Purple 76C in absence of Al. They develop in the early summer.

Leaf: The leaves, in opposite arrangement, are ovate in shape with acute base and acuminate apex and serrulate margin. The mature leaf is 9.9 cm long by 7.5 cm wide, very thick and leathery and very waxy. It has no pubescence. The color of the emerging leaf is yellow-Green 144A on the upper surface and Yellow-Green 144C on the lower surface, maturing to Green 139A on the upper surface and Green 137B on the lower. The venation is pinnate, with Yellow-Green 144D veins. The petioles average 2 cm long and 3 mm in diameter are grooved above and rounded below, with no pubescence, and are Yellow-Green 146B in color.

Inflorescence: The bloom period is mid May to the end of June in Athens, Ga., and the mature, green inflorescences persist into the fall. The corymb lacecap inflorescence contains 3 rows of sterile florets, often intermingled with fertile flowers, around the center of fertile flowers. It is oval in cross-section, 12.5 cm by 14.7 cm, and 7 cm deep. There are on average 6 inflorescences per 2-year-old plant, and the inflorescence contains 1368 flowers.

Sterile florets: There are 4 sepals per floret, and an average of 20 florets per inflorescence. The sepal is ovoid to round in shape with rounded apex and acute base and mainly entire margin with an occasional serration. The texture is smooth with no pubescence. They are 25 mm long by 23 mm wide. At peak of bloom the upper surface is Violet 84C, both in presence and absence of Al, aging to Yellow-Green 145B, and the lower surface is White N155D, both in presence and absence of Al, aging to Yellow-Green 145B. The peduncle is finely pubescent, 1 cm long and Greyed-Purple 184B in color, both in presence and absence of Al.

Fertile flowers: The 5 petals are ovate in shape, with acute apex, truncate base and an entire margin. They are 4 mm in length by 2 mm wide, with a smooth texture and no pubescence. The color of the upper surface is Violet-Blue 98B in presence of Al, and Purple 75B with Violet 85B at base in absence of Al. The lower surface is Violet-Blue 98D with Violet-Blue 98B at base and along margins in presence of Al, and Purple 75C with Violet 85B at base in absence of Al. The pedicle is 2 mm long, smooth, and Red-Purple 60A in presence of Al, and Red-Purple 58A in absence of Al. There are 10 stamens, the anthers being 1 mm long by 1 mm wide and Violet-Blue 98C in presence of Al, and Purple 76B in absence of Al. The filament is 3 mm long by 0.3 mm wide and Violet-Blue 98B/Violet-Blue 94C in presence of Al, and Red-Purple N74D in absence of Al. The superior pistil is globose in shape, 3 mm long by 2 mm wide with no pubescence. There are 3 to 4 oval stigmas per flower, finely pubescence and Violet-Blue 90A in presence of Al, and Purple-Violet N80C in absence of Al. The style is tubular in shape, 1 mm long with no pubescence and Violet-Blue 94D in presence of Al, and Purple 75B in absence of Al.

Fruit: The fruit is a capsule, oval in shape, 4 mm long by 3 mm wide, and Yellow-Green 143A in color. Seed: The seeds average 0.5 mm long by 0.25 mm wide and are Greyed-Orange 164C in color.

I claim:

1. A new and distinct variety of *Hydrangea macrophylla* plant substantially as herein described and illustrated.

* * * * *